United States Patent [19]

Chou

[11] Patent Number: 5,056,163
[45] Date of Patent: Oct. 15, 1991

[54] SWEAT-ABSORBING STRIP FOR SPORT GOGGLES

[76] Inventor: Chih T. Chou, 4, Hsin-I South Rd., Tainan City, Taiwan

[21] Appl. No.: 523,357

[22] Filed: May 15, 1990

[51] Int. Cl.⁵ .............................................. A61F 9/02
[52] U.S. Cl. .......................................... 2/453; 2/431; 2/452; 2/181
[58] Field of Search .................... 2/453, 452, 428, 430, 2/431, 438, 440, 447, 10, 181, 183, 426; 351/155, 59

[56] References Cited

U.S. PATENT DOCUMENTS 2,625,855  1/1953  Gaylor ................................ 2/453 X
4,616,367  10/1986  Jean, Jr. et al. ..................... 2/453 X
4,901,374  2/1990  Van der Woude ..................... 2/453

Primary Examiner—Peter Nerbun
Attorney, Agent, or Firm—Fleit, Jacobson, Cohn, Price, Holman & Stern

[57] ABSTRACT

A sweat-absorbing strip for a sport goggle comprises a supporting strip enveloped with a cloth cover and a horizontal supporter fixed on the sport goggle. The supporting strip has a long rectangular shape and a base having a length-wise round groove to engage with an outer round section of the horizontal supporter so that the supporting strip can be adjusted in its angle relative to the forehead of a user to rest the sweat-absorbing strip on the user's forehead.

3 Claims, 2 Drawing Sheets

SWEAT-ABSORBING STRIP FOR SPORT GOGGLES

BACKGROUND OF THE INVENTION

Common sport goggles are used for protecting user's eyes from exposure to miscellaneous airborne particulate matter. Some such goggles are provided with a sweat strip on the goggle frame to absorb perspiration during use due to physical activity.

Different users, however, have differently shaped heads. The ideal angle of forehead engagement of the sweat-absorption strip for different users can thus be quite different. Since the proper angle of strip-forehead engagement is critical to optimum effectiveness and user comfort, it is desirable to have a goggle strip design which can accommodate generally the foreheads of the majority of users. Such a design reduces or eliminates the necessity of producing many different sizes and shapes of goggles, thus enabling a manufacturer to produce a uniform product.

SUMMARY OF THE INVENTION

The sweat-absorbing strip for a sport goggle in the present invention comprises a supporting strip of a long rectangular shape attached with a base at its back and substantially enveloped by a cloth cover to absorb sweat. The base has a lengthwise round groove.

A horizontal supporter is fixed at the upper section of a goggle frame, having a round section at its outer sidewise edge to engage with the round groove in the base of the supporting strip such that this sweat-absorbing strip can be assembled with a sport goggle and rotated to adjust its angle relative to the forehead of a user.

DETAILED DESCRIPTION OF THE INVENTION

Figure 1:
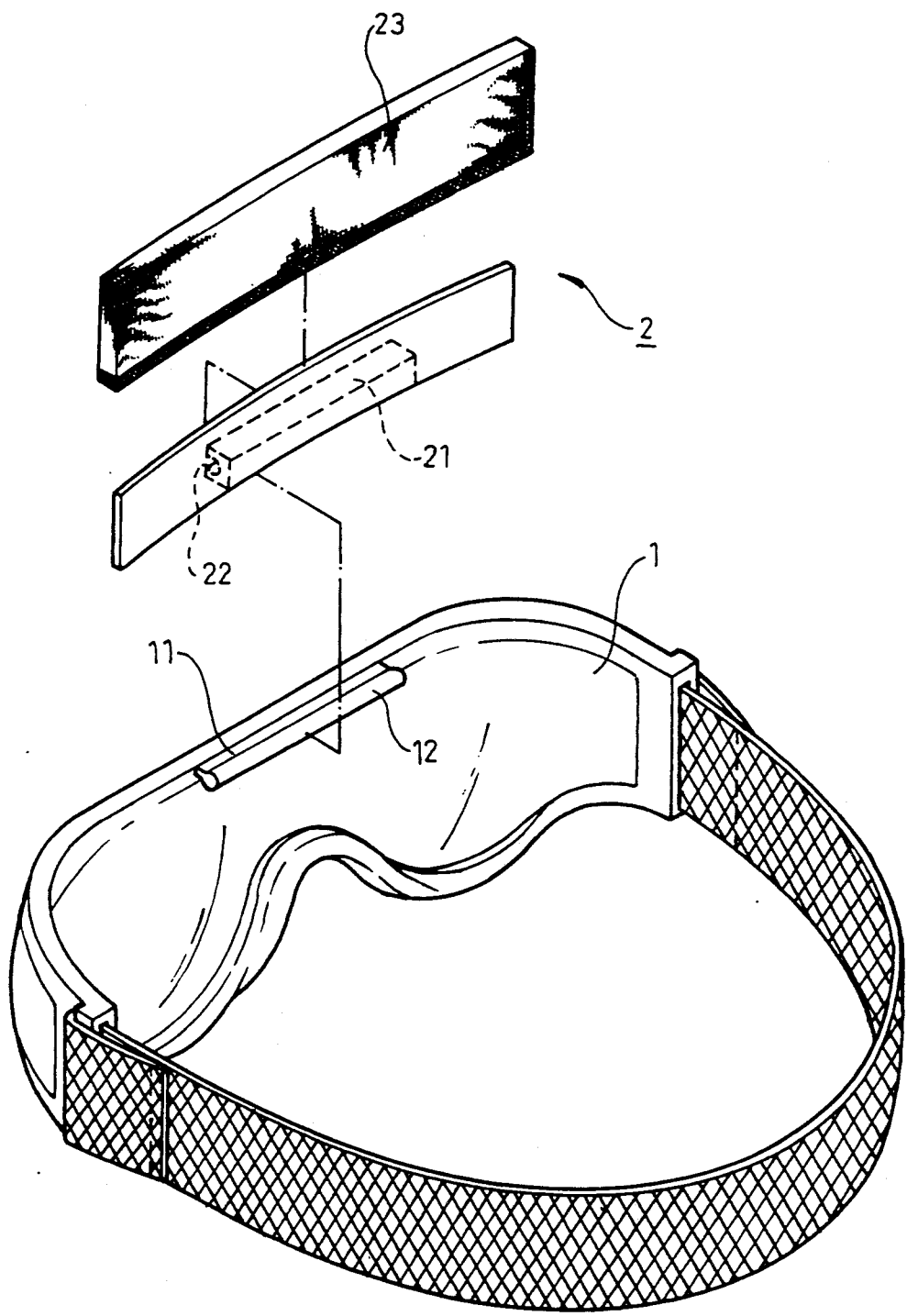
FIG. 1 is an exploded perspective view of the sweat-absorbing strip for sport goggles in the present invention.

As shown in FIG. 1, the sweat-absorbing strip for a sport goggle in the present invention comprises a horizontal straight supporter 11 to be fixed on the goggle frame and a supporting strip 2 to be engaged with the horizontal supporter 11.

The horizontal straight supporter 11 has a round section at its outer sidewise edge to engage with a round groove 22 in a base 21 of the supporting strip 2.

Figure 2:
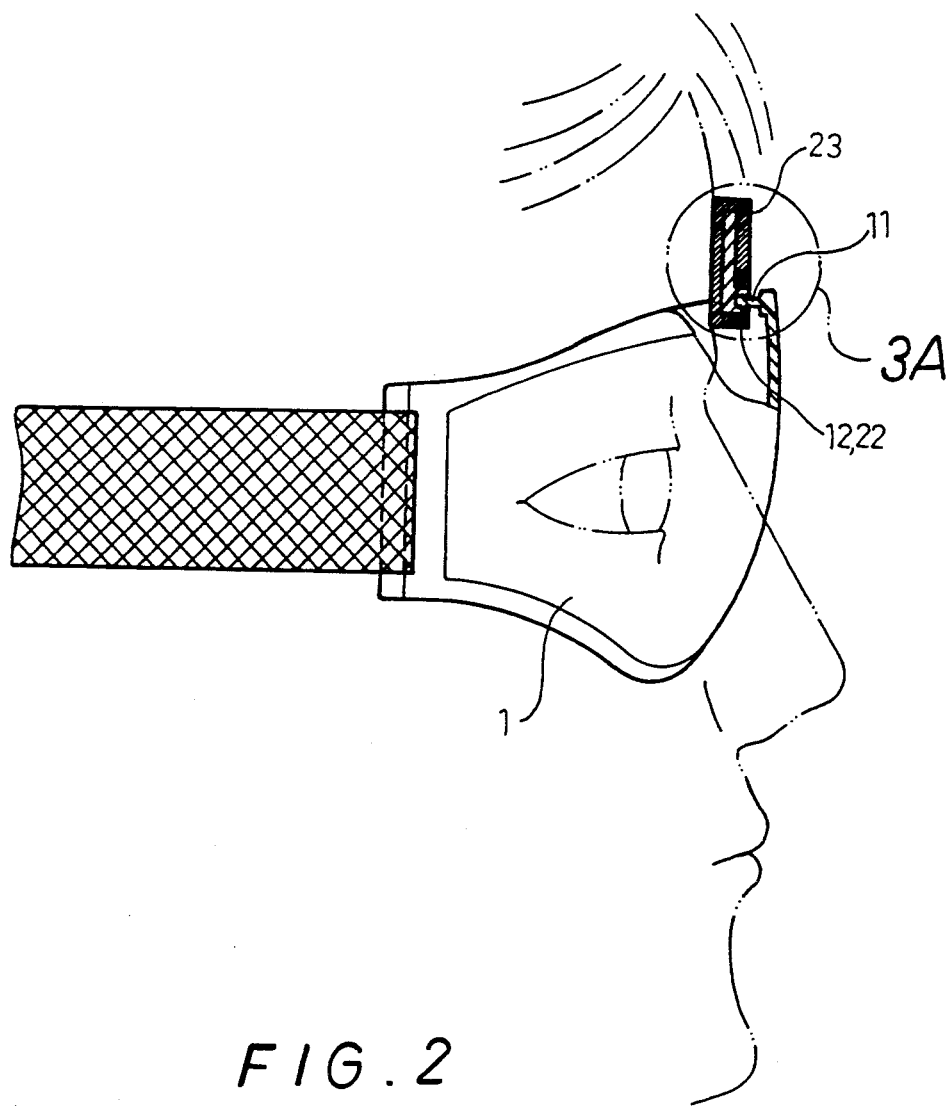
FIG. 2 is a side view and a part cross-sectional view of the sweat-absorbing strip for sport goggles in the present invention.
Figure 3A:
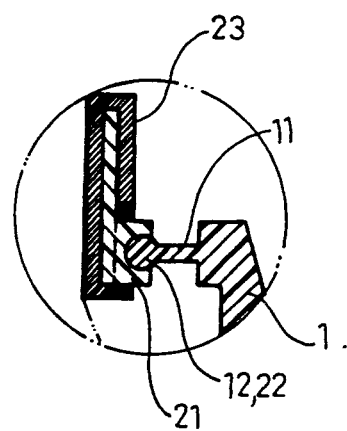
FIG. 3 is an enlarged view of the part marked 3A on FIG. 2.
FIG. 3B is a cross-sectional view of the sweat-absorbing strip being adjusted.
Figure 3B:
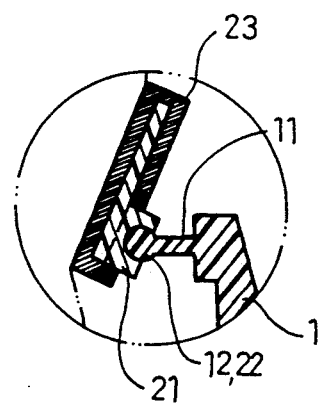

The supporting strip 2 of a long rectangular shape as shown in FIG. 2, is made of plastics and substantially enveloped with a cloth cover 23 to absorb sweat. The base 21 has a round groove 22 and is attached at the back of the supporting strip 2. The strip 2 is also made of plastics so that its round groove 22 may have some elasticity to be expanded somewhat so as to receive the round section 12 therein with ease.

After the horizontal supporter 11 is assembled with the base 21, having its round section 12 engaged with the round groove 22, the supporting strip 2 can be rotated relative to the horizontal supporter 11 to a proper angle to rest the strip 2 comfortably on the forehead of a user for absorbing sweat dripping down the forehead.

What is claimed is:

1. A sport goggle having a frame for covering a user's eyes, head-encircling means directly attached to said frame for mounting said frame in an approximately fixed position relative to the user's forehead, and a perspiration-absorbing strip assembly comprising:

perspiration-absorption means; and angularly adjustable means rotatably mounting said perspiration-absorption means on said goggle frame for rotational adjustment of the perspiration absorbing means relative to the user's forehead when the frame is mounted thereon by the head-encircling means.

2. The goggle of claim 1, wherein said perspiration-absorption means comprises a cloth cover.

3. The goggle of claim 1, wherein said mounting means comprises:

a horizontal straight supporter fixed on the goggle frame and having a round section at its outer sidewise edge, and a supporting strip of long rectangular shape having a long base fixed at the back of said strip, said base having a lengthwise round groove to receive and engage with the round section of said horizontal supporter, said supporting strip being substantially enveloped by said perspiration-absorption means, whereby an angle between said horizontal straight supporter and said supporting strip may be adjusted to conform the angular position of said strip to an optimum strip-forehead engagement angle with the user's forehead.

* * * * *